United States Patent [19]
Amann et al.

[11] Patent Number: 6,124,088
[45] Date of Patent: Sep. 26, 2000

[54] METHOD OF PERMANENT REMOVAL FROM CELL SUSPENSION IN A POROUS CONTAINER

[75] Inventors: Rupert P. Amann, Fort Collins, Colo.; Roy H. Hamerstedt, Boalsburg, Pa.

[73] Assignee: BioPore, Inc., State College, Pa.

[21] Appl. No.: 09/136,556

[22] Filed: Aug. 19, 1998

Related U.S. Application Data

[60] Provisional application No. 60/056,607, Aug. 20, 1997.

[51] Int. Cl.$^7$ ........................................... A01N 1/02
[52] U.S. Cl. .................. 435/2; 435/374; 435/1.3
[58] Field of Search .................. 435/1.1, 1.2, 1.3, 435/2, 374

[56] References Cited

U.S. PATENT DOCUMENTS

| | | | |
|---|---|---|---|
| 3,881,990 | 5/1975 | Burton et al. | 195/1.7 |
| 4,004,975 | 1/1977 | Lionetti et al. | 195/1.8 |
| 4,251,995 | 2/1981 | Pert et al. | 62/60 |
| 4,471,629 | 9/1984 | Toledo-Pereyra | 62/64 |
| 5,026,342 | 6/1991 | Hamerstedt et al. | 600/35 |
| 5,160,312 | 11/1992 | Voelkel | 600/34 |
| 5,261,870 | 11/1993 | Hammerstedt et al. | 600/35 |
| 5,309,723 | 5/1994 | Thomas et al. | 62/62 |
| 5,595,866 | 1/1997 | Critser et al. | 435/2 |
| 5,691,133 | 11/1997 | Critser et al. | 435/2 |
| 5,700,632 | 12/1997 | Critser et al. | 435/2 |
| 5,723,282 | 3/1998 | Fahy et al. | 435/1.3 |
| 5,753,427 | 5/1998 | Critser et al. | 435/2 |
| 5,776,769 | 7/1998 | Critser et al. | 435/307.1 |

OTHER PUBLICATIONS

Verheyen et al., "Effect of freezing method, thawing temperature and post–thawing dilution/washing on motility (CASA) and morphology characteristics of high–quality human sperm", Human Reproduction 8 (10) : 1678–84 (1993).

"Cryopreservation," Benson, pp. 147–167 (1994).

*Primary Examiner*—Sandra E. Saucier
*Attorney, Agent, or Firm*—Webb Ziesenheim Logsdon Orkin & Hanson, P.C.

[57] ABSTRACT

A process and apparatus in which cryoprotectant in cryopreserved samples is removed with the use of turbulence and convective-dispersion around the cells within the primary cryopreservation container. Convective-dispersion is applied via the combined action of gravity and pulsatile transmembrane flow of buffer through the pores of containers fabricated from appropriate membrane material such as that disclosed in U.S. Pat. No. 5,026,342 and U.S. Pat. No. 5,261,870, as incorporated herein by reference above. By using mechanical forces to aid the process of cryoprotectant removal, the benefits of slow cryoprotectant removal are retained while the actual removal time is markedly decreased.

7 Claims, 9 Drawing Sheets

METHOD OF PERMANENT REMOVAL FROM CELL SUSPENSION IN A POROUS CONTAINER

RELATED APPLICATIONS

This application is based on priority Provisional Application Serial No. 60/056,607, filed Aug. 20, 1997 of which the following specification is a Continuation-in-Part.

RIGHTS IN THE INVENTION

This invention was made with Government support under Grant 1R43-HD-35409-01 awarded by the National Institutes of Health. The Government has certain rights in the invention.

FIELD OF THE INVENTION

The present invention relates to mechanically assisted methods, and apparatus therefor, to remove cryoprotectant from suspensions of cells in need of cryoprotection.

BACKGROUND OF THE INVENTION

Cryopreservation is a procedure for preparation of a suspension of cells, or a group of cells such as an embryo, for storage. The procedure normally incorporates adding cryoprotectants to the cells to be preserved, cooling of the suspended cells, long-term storage of the cell suspension at temperatures below about −80° C., warming of the cells to normal cell temperatures, and removal of cryoprotectant from the cells. Cryopreservation of sperm or other cells from common mammals is a deceptively simple-appearing process which succeeds despite certain serious obstacles. This success depends on the use of one or more cryoprotectants in the context of certain procedural parameters.

Overall cryopreservation procedures thus generally include: preparation of a suspension of cells for low-temperature storage by incorporation of cryoprotectants, and placement of individual units into vials or "straws"; cooling (sometimes called "freezing") at an appropriate rate; long-term storage of the suspension of cells at a temperature lower than −80° C. and often between −180° C. and −196° C.; distribution at low temperature to intermediaries or users; warming (sometimes called "thawing") at an appropriate rate to the normal cellular temperature; and controlled removal of cryoprotectant plus any other medium or other adjustments needed to render the cells ready for in vivo use. The goal is not just to keep cells alive (viable), but to optimize retention of all cellular attributes such as normal life span, oxygen-carrying potential (especially in the case of erythrocytes) and fertilizing potential (in the case of spermatozoa or oocytes), for which the cells are being preserved in the first place.

Notwithstanding cell type, species of origin or the various protocols used, prior art cryopreservation protocols traditionally result in about 30% mortality (or worse) of cells being preserved. Many cells traditionally did not survive the cooling and rewarming, and those which did suffered further damage during removal of the intracellular cryoprotectant. Damage can result from any or all of improper rates of temperature changes during cooling and rewarming, formation of ice crystals, reduction in temperature per se, toxicity due to high concentrations of solutes within and around the cells, the nature and concentration of the cryoprotectant(s) used, rates of addition and removal of cryoprotectants from within the cells, and other lesser known but empirically evident factors.

A cryoprotectant is a molecule which allows a substantial percentage of cells to survive a freeze-thaw cycle and to retain normal cell function. Cryoprotectants which pass through the cell plasma membrane, and which thus act both intracellularly and extracellularly, are termed penetrating cryoprotectants. Non-penetrating cryoprotectants act only extracellularly. Glycerol is the most effective penetrating cryoprotectant for certain types of cells and for sperm from most species. Glycerol is of low toxicity, relative to the alternative penetrating cryoprotectants such as ethylene glycol, propylene glycol and dimethylsulfoxide. All penetrating cryoprotectants pass through a cellular membrane at a rate slower than water does, and each of these rates is itself temperature dependent. Non-penetrating cryoprotectants include proteins (such as milk or egg proteins used with mammalian sperm); sugars such as lactose, fructose, raffinose or trehalose; synthetic polymers such as methyl cellulose; and amide compounds. Most penetrating cryoprotectants, such as glycerol, serve as a solute (and cause osmotic flow of water) and a solvent (to dissolve salts and sugars) miscible with water. All non-penetrating cryoprotectants are solutes or colloids, and cannot themselves also serve as solvents. Both water and glycerol, as well as other solvents, pass through the membrane of cells and eventually equilibrate at the same concentration in all internal structures, so that the intracellular and extracellular concentrations are the same.

The solute role of a penetrating cryoprotectant is believed to cause damage due to the induced osmotic flow of water. The solvent role is beneficial, however, because the penetrating cryoprotectants such as glycerol have a freezing point much lower than that of water. In the presence of glycerol, the portion of the solvent mixture remaining unfrozen at any given temperature is greater than if water were the only solvent. Hence, at any given temperature there is more "space" for the cells in channels of unfrozen solvent and a lower concentration of solutes (the same amount of solutes is contained in more liquid). This phenomenon occurs both inside and outside the cells. Further, the presence of glycerol probably reduces formation of micro-fractures in the ice and this, in turn, minimizes damage to cells. Non-penetrating cryoprotectants, such as sugars and lipoproteins, typically are present in relatively high concentrations. They typically act by modifying the plasma membrane, so that it is more resistant to temperature-induced damage, or simply by acting as a solute to lower the freezing point of the solute/solvent combination.

Conventional procedures for preservation of many cells involve abrupt addition of a penetrating cryoprotectant, such as glycerol, to a cell suspension despite both long-standing and recent warnings that penetrating cryoprotectant should be added slowly. Similarly, the benefit of slow removal of penetrating cryoprotectant from cells is well known. Damage associated with the rapid addition or removal of a penetrating cryoprotectant is a direct consequence of extreme changes in cell volume, resulting from rapid movement of water, and formation of irreversible "tears" in the plasma membrane. Slow removal of cryoprotectants from within thawed cells generally has not been used, either because of ignorance or lack of a convenient approach to achieve it.

Depending on the number of cells required for a functional "unit" after thawing, cells traditionally are packaged as individual units using glass ampules, plastic vials, plastic straws, or appropriately sized plastic bags. These packages all require removal of the cell suspension from the primary container before slow removal of cryoprotectant.

Alternatively, technology disclosed by Hammerstedt et al. (U.S. Pat. No. 5,026,342 and U.S. Pat. No. 5,261,870, both incorporated herein by reference) allows slow removal of cryoprotectant while the cells remain within the primary container, via open pores in a special membrane formed to provide a primary container which allows exchange of fluid across the membrane. Although efficacious, because this approach is diffusion-limited the process can require up to two hours to reduce the concentration of cryoprotectant within the cells to a desired level.

Apart from the widely practiced stepwise dilution used to address this problem, slow removal of cryoprotectant from cells in a suspension can be accomplished by placing the suspension, after thawing, into a conventional dialysis membrane and suspending the dialysis unit in a large volume of a salts solution. Alternatively, special plugged-pore containers, such as those disclosed in the U.S. patents incorporated by reference above, can be processed after thawing in a manner to open the pores of the membrane-container and to allow movement of molecules across the membrane. In both cases, movement of cryoprotectant or water through the membrane of the primary container is via diffusion and "down" the concentration gradient (i.e., away from the locus of highest concentration). Such diffusion-based processes effectively limit the rates at which composition of the medium immediately surrounding the cells is altered as water and cryoprotectant diffuse, in and out respectively, across the primary container membrane. Consequently, this limits rates of movement of water and cryoprotectant across the membranes of the cells to flux degrees which are not damaging to the cells. Reliance on simple diffusion through the membrane container requires a commercially unacceptably long 1–2 hour time period.

The alternative assisted cryoprotectant removal method uses continuous flow centrifugation, such as is discussed in U.S. Pat. No. 4,221,322. This requires transfers from the original cryopreservation packaging, thus affording opportunity for contamination and requiring excessive processing.

A need thus remains for a method for introducing and removing one or more cryoprotectants, to and from a cell or group of cells in need of cryopreservation, in which the cellular damage, potential contamination and/or long processing times of the prior art are avoided.

SUMMARY OF THE INVENTION

In order to meet this need, the present invention embodies a process and apparatus in which cryoprotectant in cryopreserved samples is removed with the use of turbulence and convective-dispersion around the cells within the primary cryopreservation container, applied via the combined action of gravity and pulsatile transmembrane flow of buffer through the pores of primary containers fabricated from appropriate membrane material such as that disclosed in U.S. Pat. Nos. 5,026,342 and 5,261,870, as incorporated herein by reference above. By using mechanical forces to aid the process of cryoprotectant removal, the benefits of slow cryoprotectant removal without transferring out of the original primary container are retained, while the actual removal time is markedly decreased and sterility maintained.

DETAILED DESCRIPTION OF THE INVENTION

Figure 1:
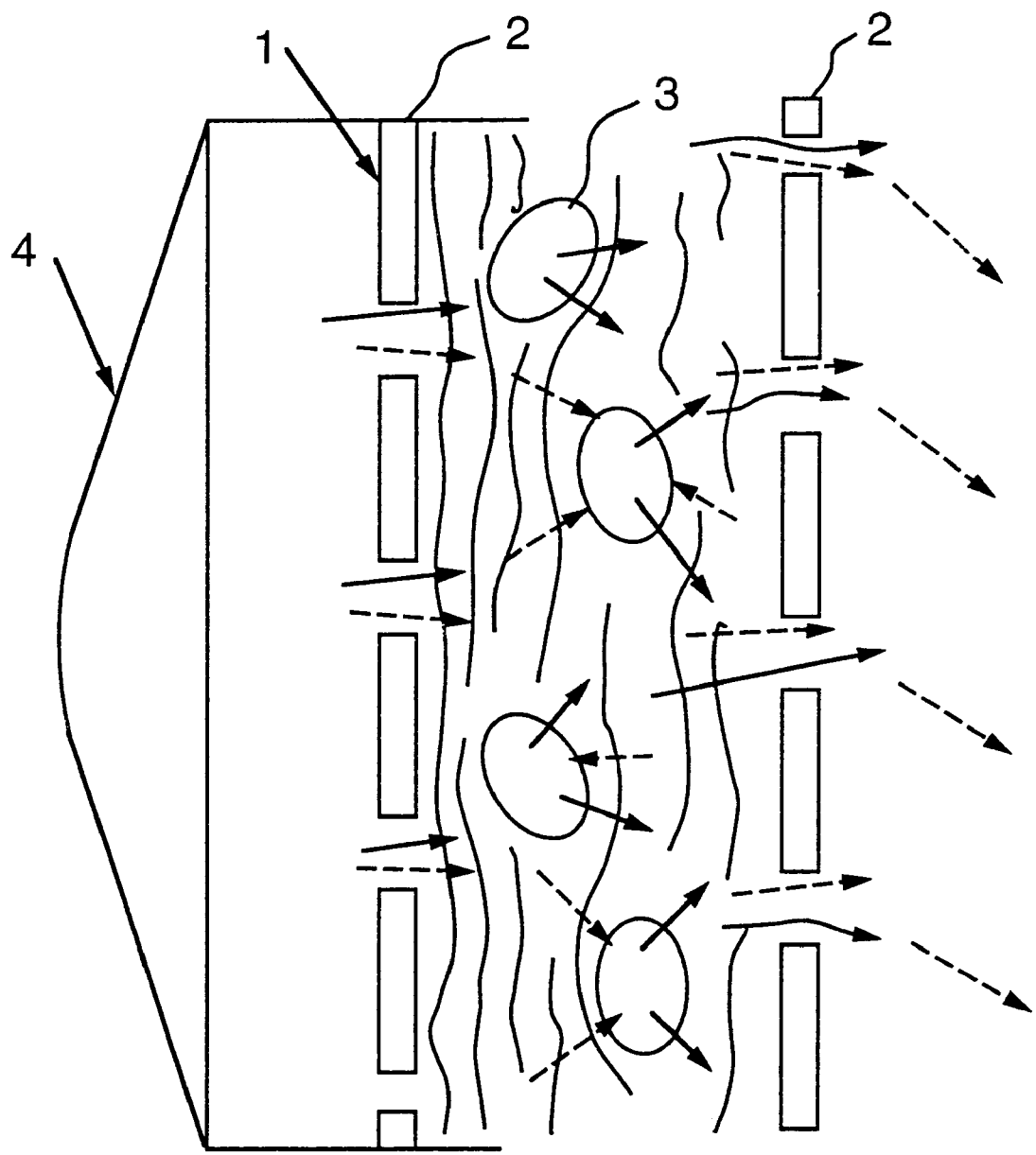
FIG. 1 is a side sectional view of a first embodiment of the present invention.

The present invention embodies a process and apparatus in which cryoprotectant in cryopreserved samples is removed with the use of turbulence and convective-dispersion around the cells within the primary cryopreservation container, applied via the combined action of gravity and pulsatile transmembrane flow of buffer through the pores of containers fabricated from appropriate membrane material such as that disclosed in U.S. Pat. No. 5,026,342 and U.S. Pat. No. 5,261,870, as incorporated herein by reference above. By using mechanical forces to aid the process of cryoprotectant removal, the benefits of slow cryoprotectant removal are retained while the actual removal time is markedly decreased.

Because of considerations of biohazard and sterility, optimally the means for providing the mechanical facilitation of cryoprotectant removal is a means not directly contacting the internal surfaces or contents of the primary container. This is particularly true in the case of human cells (e.g., spermatozoa, oocytes, embryos, fetal cells or blood cells), any or all of which should not be allowed to come in contact with the technician or other operator handling the containers. The following description presents two versions of a new device for rapidly reducing the concentration of cryoprotectant, within a separate container configured according to U.S. Pat. No. 5,026,342 and U.S. Pat. No. 5,261,870, by the combined use of gravity, turbulence and convective-dispersion.

For certain types of cells (e.g., erythrocytes) destined for infusion into the vascular system or other body compartments, maintenance of sterility throughout the freeze-thaw and cryoprotectant removal process is desirable, but currently difficult. Cryoprotection can not be removed while the cells are within the original blood cell storage bag. For that reason, the FDA restricts the interval between thawing and deglycerolation of human erythrocytes and their infusion into humans to 24 hours. The primary problem is the need to transfer the thawed cells from a primary container (plastic bag) for freezing to a disposable system for cryoprotectant removal which includes interconnected containers of sterile buffer, a centrifuge bowl and cell-receiver. Similar problems hamper cryopreservation of other cell types. Hence the present invention provides in part for a single device in which a primary container stores the cell suspension and additional components enable rapid removal of cryoprotectant by combined actions of gravity, turbulence and convective-dispersion. The primary container also enables maintenance of sterility throughout the entire freeze-thaw and cryoprotectant removal process, and does not dilute the cell suspension.

The present process is best understood in the context of the simple diffusion over which it represents an improvement. Traditionally, conventional dialysis devices containing cells and cryoprotectant, or primary containers fabricated as in patents incorporated by reference herein were diffused in buffer to remove the cryoprotectant through small pores or other membrane transport interstices provided in the walls of the vial or straw. When buffer flow was provided continuously outside the container of cells, the cryoprotectant concentration in the flowing buffer remained low and the cryoprotectant in the cell suspension predictably passed "down" the concentration gradient across the porous wall of the container, and into the external buffer.

By contrast, the present process does not rely on simple diffusion across the container wall for removal of cryoprotectant. Further, simple diffusion of cryoprotectant across the cell plasma membrane is facilitated by convective-dispersion within the primary container. This is achieved via an appropriate blend of the processes of turbulent flow and diffusion through a porous membrane, created by pulsatile applications of pressure to transport fluid into and through the primary container. Inside the primary container, the turbulent flow and convective-dispersion of cryoprotectant-free buffer in cryoprotectant-rich buffer results in global spreading of inhomogeneity, as aided by gravity acting on the relatively dense cryoprotectant, modifies the microenvironment near a cell in a controlled manner. The extent of mixing is controlled, in part, by: the frequency and volume of pulses of cryoprotectant-free buffer entering the primary container; the zone of buffer entrance and/or penetration relative to the lower or upper portions of the contents within the primary container (due to the natural settling of cryoprotectant-rich buffer to the bottom of the container); orientation of the "entrance" membrane of the primary container (because gravity can affect redistribution and dispersion of cryoprotectant-rich buffer within the chamber); and optional movement of the primary container induced by mechanical means. Pulsatile flow can be applied with only inward pressure, allowing minor retrograde flow during the inter-pulse interval, or with a combination of inward and withdrawal pressures—positive and negative flow—directly inducing both direct and retrograde flow.

Parameters were developed as follows. Assuming that removal of cryoprotectant by diffusion requires 6 container volumes (6×1 ml) of buffer over a thirty minute period, minimum flow rate to accomplish the same cryoprotectant removal would require 0.2 ml/min and a flow rate of 1–3 ml/min would accomplish the task in under twelve minutes assuming actual flow of buffer during one-half (direct flow) of the elapsed time. Under these conditions, mass transfer is not limited by the transport rate associated with diffusion of cryoprotectant from the primary container and then the cells. Rather, mass transfer out of the primary container and mixing of cryoprotectant-rich with cryoprotectant-free buffer within the primary container occur via convective-dispersion, and cryoprotectant moves out of the cells by simple diffusion down a concentration gradient changed at an appropriate rate by convective-dispersion. The convective-dispersive transport of cryoprotectant will display approximately equal dependence on convection and diffusion at a flow rate of approximately 1.2 ml/min, assuming a membrane area of approximately 4 cm$^2$, with increasing dependence on diffusion at slower flow rates. To minimize accumulation of cells on the down-stream membrane face, and to facilitate occurrence of convective-dispersion, an oscillating (start/stop) flow is used; the pulsatile flow can range from 1 to >60 pulses/min, but oscillation frequencies of 2–40 pulses/min often is appropriate. Further, it is often advantageous to initiate cryoprotectant removal with low frequency (e.g., 1–2 pulses/min) and low volume (e.g., 0.05–0.1 ml) pulses and gradually increasing the pulse frequency, pulse volume or both in a "ramp-like" manner. This reduces the concentration of cryoprotectant in the microenvironment of a cell at a rate which is non-damaging to the cell, but which facilitates diffusion of cryoprotectant out of the cells in a commercially viable time frame. Hence, the process provides an appropriate blend of turbulent flow, convection and diffusion to provide global spreading of inhomogeneity of the fluid environment near a cell in a controlled manner. With such approaches, cryoprotectant can be safely removed from cells in a 1-ml container in less than 15 minutes.

The preferred embodiment of the present invention is a cryoprotectant removal device designed to accommodate a separate primary container incorporating two major faces fabricated from membranes as disclosed in the above-incorporated patents. At the time of cryoprotectant removal, a turbulent flow of small volumes of buffer is applied through the open pores of the primary container and via convective-dispersion within the primary container a gradual mixing of cryoprotectant-free and cryoprotectant rich buffer ensues, with the slow discharge thereafter of diluted cryoprotectant out of the primary container. To induce appropriate turbulence and convective-dispersion, and also to minimize accumulation of cells on the down-stream membrane face, an oscillating (start/stop) flow of cryoprotectant-free buffer is used. Hence, the device provides an appropriate blend of the processes of turbulent flow, convection and diffusion to provide global spreading of inhomogeneity of the fluid environment near a cell in a controlled manner. This reduces the concentration of cryoprotectant in the microenvironment of a cell at a rate which is non-damaging to the cell, but which facilitates diffusion of the cryoprotectant out of the cell.

The simplest device according to the present invention is shown in FIG. 1. A primary container 1 containing walls 2 having pores therein and including cryoprotectant-containing cells 3 inside the walls 2 is infused with buffer by means of an exterior compression diaphragm 4. The exterior compression diaphragm 4 is powered by any known means such as cyclic vacuum to give pulsatile compression of the buffers into and out of the primary container 1. The inward pulsatile pumping of buffer and the resultant convective-dispersion which takes place inside the primary container 1 changes the cryoprotectant concentration within the cells 3 and within the container 1 more rapidly than could simple diffusion, but at a rate still tolerated by the cells 3. Movement of water into and cryoprotectant out of the cells 3 is by diffusion across the cell plasma membrane, and the concentration gradients are steeper than with conventional methods.

Figure 2A:
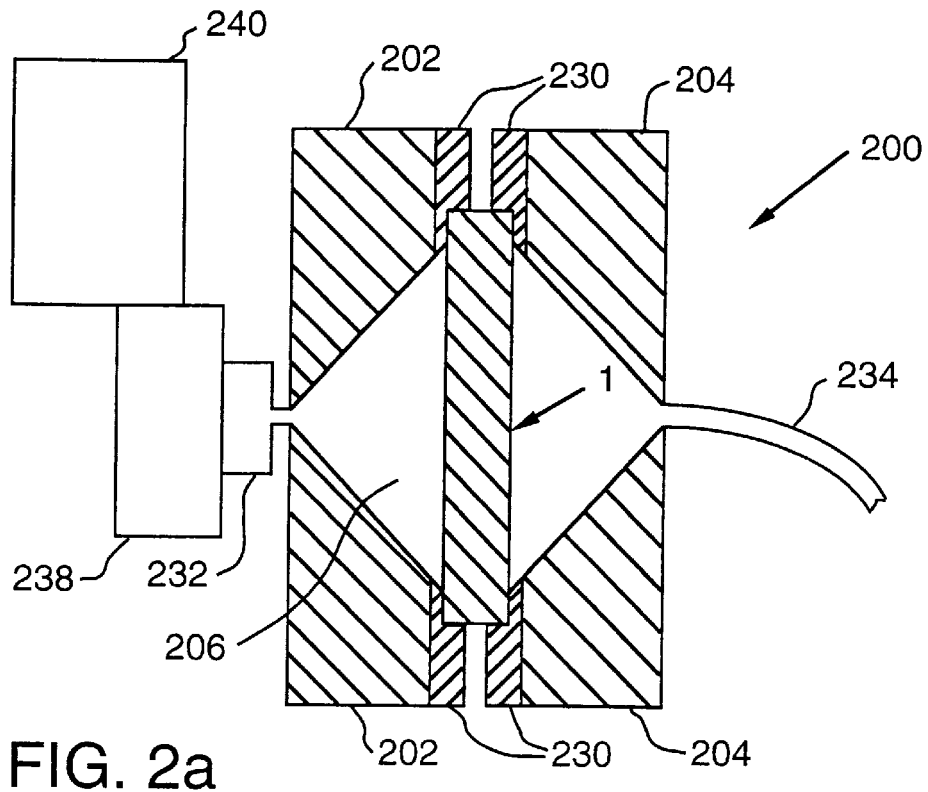
FIGS. 2a and 2b are side sectional views (the latter in dissembled form) of a second embodiment of the invention.
Figure 2B:
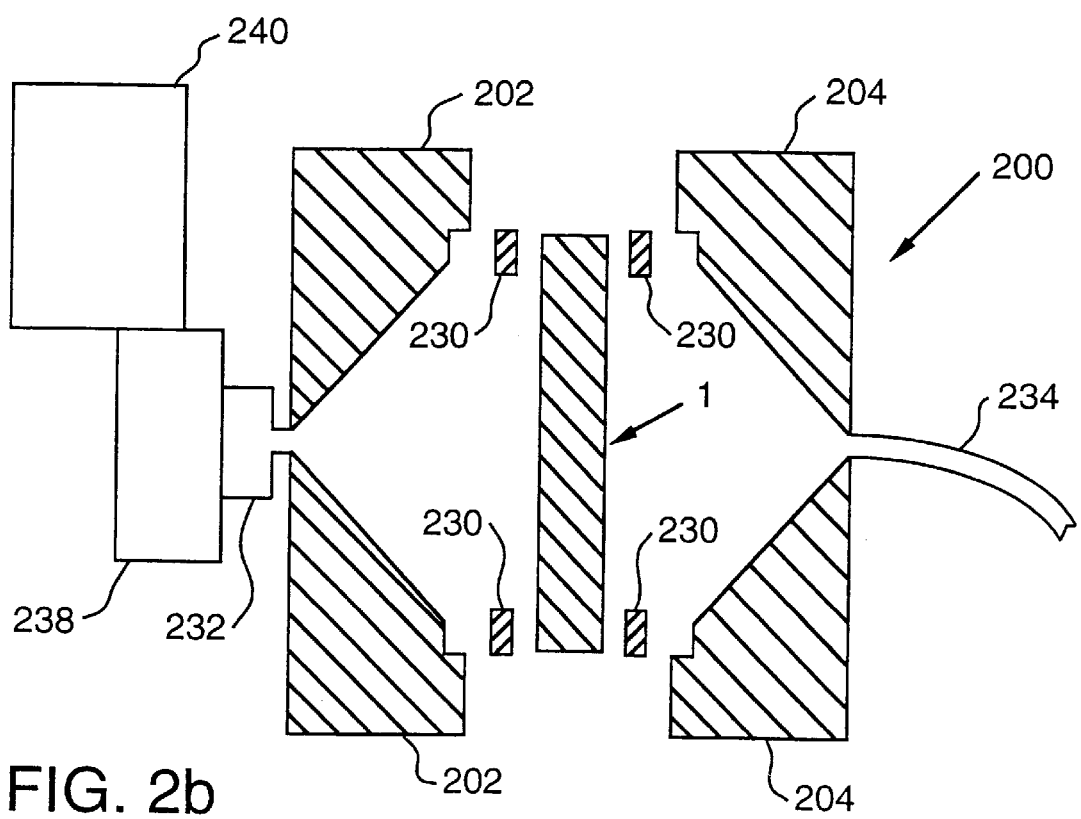

A second embodiment of the present cryoprotectant removal device is shown in FIGS. 2a and 2b. FIG. 2b shows the same structures as appear in FIG. 2a, but in dissembled array. The same primary container 1 as shown in FIG. 1 is shown in position within a split cube device 200. The primary container is a porous container whose previously plugged pores are now, at the time of cryoprotectant removal, open according to means disclosed in U.S. Pat. No. 5,026,342 and U.S. Pat. No. 5,261,870 and by other means known in the art. The split cube device 200 has two chambers 202 and 204 describing inflow chamber 206 and outflow chamber 208, respectively. A pair of gaskets 230 seal the chambers around the primary container 1. The chambers 206 and 208 are connected to inlet port 232 and outlet port 234 as illustrated. The inflow chamber 206 is connected via the inlet port 232 to a pump 238 capable, by means of a controller known to those skilled in the art, of delivering a programmed sequence of pulses of desired buffer, with each pulse having a specific volume, duration, duty cycle and inter-pulse interval. Buffer is drawn from the reservoir 240 by the pump 238, is passed into the inflow chamber 206, from thence through the primary container 1, and out through the outflow chamber 208 and the outlet port 234 for recycling.

The structures of FIGS. 2a and 2b are generally plastic or polymer prepared by various means including sheet fabrication, injection molding, or any other method. Other materials such as metal or glass or other composites may also be used. In operation, and depending on the characteristics of the primary container and the cells therein, positioning of the split cube device will provide the desired orientation of the porous surfaces of the primary container 1 and the optimal direction of the buffer flow into and through the primary container 1. With some cell types it is advantageous to orient buffer flow into the lower region of the primary container 1, so that gravity can aid in mixing cryoprotectant-rich and cryoprotectant-poor buffer within the primary container 1. Additional movement of the split cube device 200 by any known means, but within defined parameters, further enhances convective-dispersion within the primary container 1.

A more complex rapid cryoprotectant removal device is designed for a particular application such as removal of cryoprotectant from human sperm frozen and thawed in a CryoCell® container according to U.S. Pat. No. 5,026,342 or U.S. Pat. No. 5,261,870. A system for this application addresses the provision of: (a) a one-time use of a sterile, integral unit containing necessary buffer, collecting waste, and allowing easy disposal as a biohazard; (b) complete automation via microprocessor control upon placement of the primary container 1 in the device; (c) fluid flow parallel to the membrane faces of the primary container 1 while the plugged pores open, followed by slow and controlled turbulent transmembrane flow thereafter; (d) controlled addition of desired additives; and (e) temperature control with optional warming, in addition to commercial features such as attractive features and minimized cost.

Figure 3:
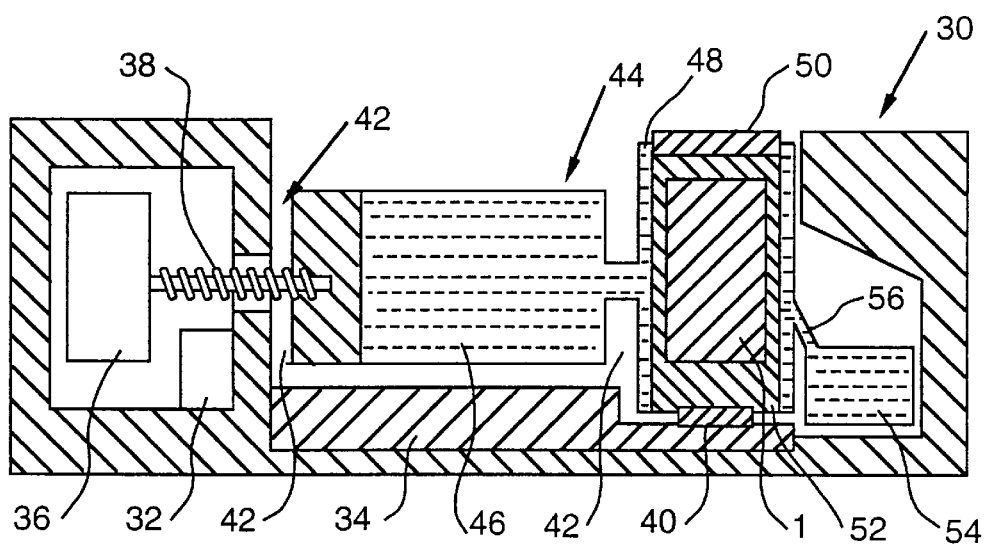
FIG. 3 is a side sectional view of a third embodiment of the present invention.

In furtherance of such a specialized system, a third embodiment of the invention is shown in FIG. 3. An overall housing 30 incorporates a microprocessor controller 32, a thermoelectric cooler 34, piston driver 36 and piston 38 as a mechanical means of creating pulsatile flow, a cam driver 40, a receptacle 42 formed as a recess in the housing 30 to accept a disposable insert 44. The receptacle 42 is temperature controlled and shaped to position the disposable insert 44 firmly against the piston 38 and the spring-loaded cam driver 40. The disposable insert 44 contains buffer reservoir 46 and is attached as a unit to the treatment chamber 48 having a removable cap 50 and a sleeve 52 adapted to receive a primary container 1 according to FIG. 1. The primary container 1 can be rotated within the sleeve 52 at 90° about its own vertical axis, to reorient the membrane surfaces of the primary container 1 with respect to the direction of buffer flow. The spring loaded cam driver mates with the primary container 1 to facilitate this rotation, which can alternatively be performed manually in when the cam driver 40 is not present. A waste container 54 with a vent maintaining sterility is connected to the treatment chamber 48 by a waste tube 56, and all can be integral to the disposable insert 44.

In the third embodiment of the invention, the disposable insert 44 and its associated structures can be sterile to begin with, and with both sterility and disposability the possibility of cross-contamination of samples is minimized or eliminated. Disposable single units such as this always minimize biohazard exposure to personnel, as well. Piston driver 36 may be a stepping motor, solenoid-driven micro-pump, or other force exertion means known in the art. In operation, pulse rate and buffer volume can either be constant or more preferably begin at a pulse rate of from 1–3 pulses per minute to increase to a pulse rate in excess of 10 pulses per minute over a total interval of 2 to 10 minutes. Flow can also optimally be increased from an initial flow rate of about 0.05–0.1 ml per pulse to 0.1–0.2 ml per pulse over the same 8 to 10 minute interval.

The disposable insert 44 may be configured so that treatment chamber 48 is sealed with a peel-away closure (outer layer) known in the art. After removal of the seal, the cap 50 is removed and the primary container 1 is inserted into the sleeve 52 in a position to provide for initial buffer flow parallel to the membrane surfaces of the primary container 1. Buffer control is provided by the microprocessor 32, the piston driver 36 and the piston 38, with the microprocessor implementing preset pulse and volume rates. After a predetermined time, the primary container 1 can be rotated (either manually or by microprocessor guidance) within the treatment chamber 48 at 90° relative to its own vertical axis, optionally in conjunction with rotation of the spring loaded cam driver 40, to create a normal (perpendicular) buffer flow with respect to the porous surface, rather than a parallel flow. After buffer treatment is complete, ready lights and ready alarms may be used to assure that the primary container 1 is removed for further appropriate handling. The entire process requires less than 30 minutes. Because only 2–3 minutes is required to replace the disposable insert 44 in the housing 30, as few as 2–4 units described in the third embodiment would provide enough equipment even for a high volume clinic.

Figure 4A:
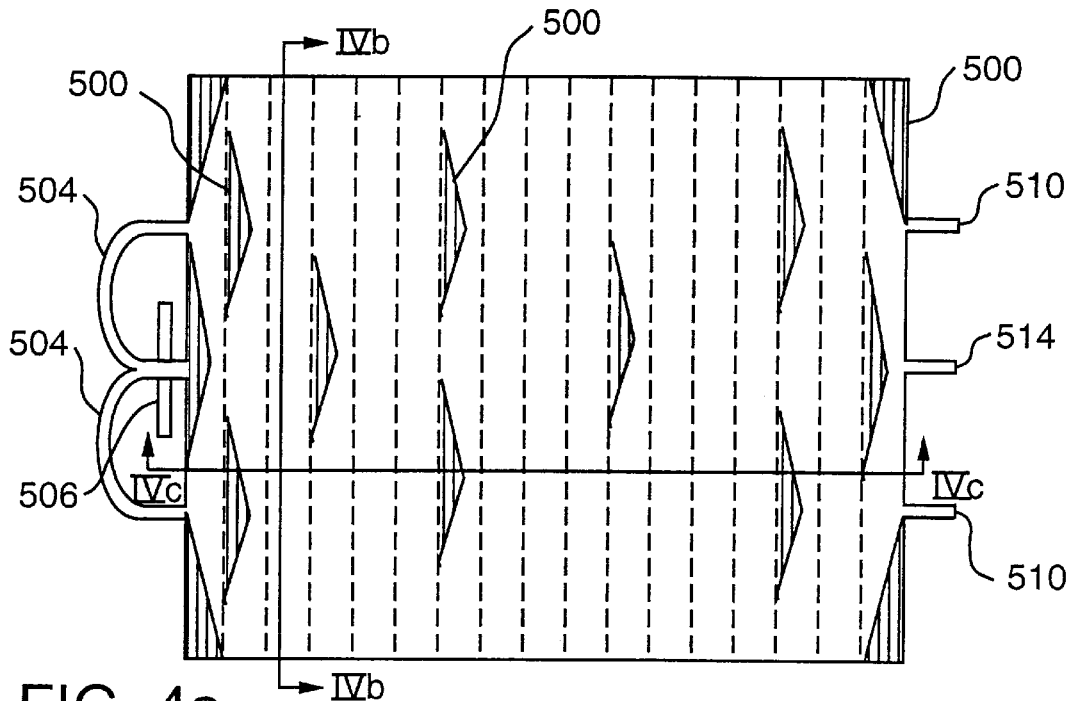
FIGS. 4a, 4b and 4c are plan, end sectional and side sectional views, respectively, of a fourth embodiment of the present invention.
Figure 4B:
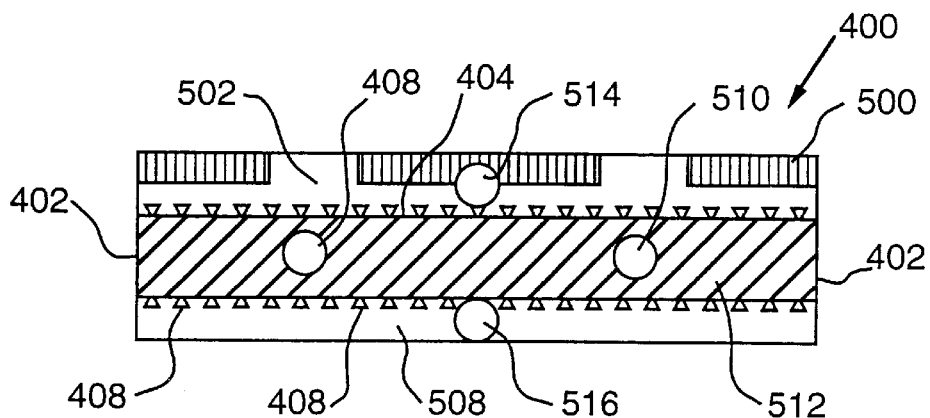
Figure 4C:
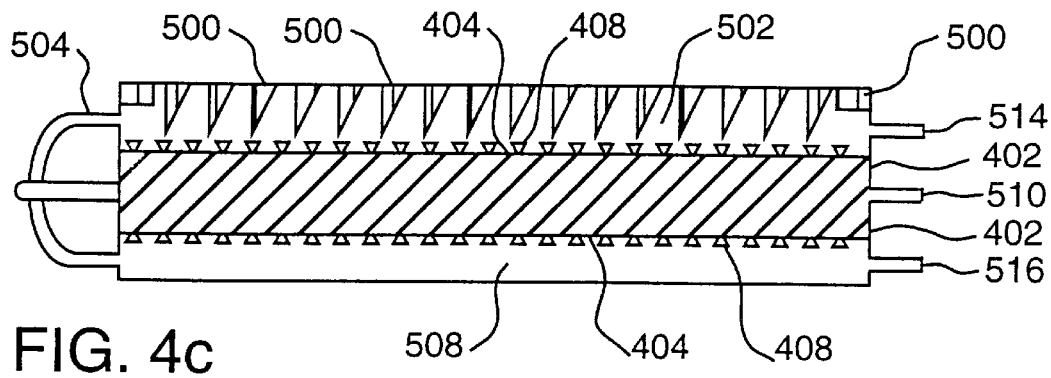

A fourth embodiment of the invention addresses an alternative to the spring-loaded cam rotation discussed above to redirect buffer flow from parallel to normal (perpendicular with respect to the member surface). A fourth embodiment of the present apparatus is shown in FIGS. 4a, 4b and 4c.

For certain types of cells, such as erythrocytes, destined for infusion into the vascular system or other body compartments, maintenance of sterility throughout the freeze-thaw and cryoprotectant removal process is desirable and damage to the cells must be minimized. With prior art procedures this was difficult, because transfer of thawed cells to a counter-flow centrifugation washing system was necessary to remove cryoprotectant slowly from the thawed cells and to provide a suspension appropriate for infusion into a patient. The fourth embodiment of the present invention is adapted to address this medical challenge. A single unit combines a primary cell container, with membranes excluding most microorganisms (such as 0.2 micrometer pore size), and a rapid cryoprotectant cell removal device; the entire device is designed as a single-use, disposable item. Consequently, this device: (1) enables maintenance of sterility throughout the entire freeze-thaw and cryoprotectant removal processes; (2) provides removal of cryoprotectant by combined actions of diffusion and convection-dispersion at a rate which is conveniently short but also sufficiently slow so as not to damage the erythrocytes; and (3) allows direct infusion of processed erythrocytes from the container into the patient because it does not dilute the cell suspension or require post-thaw centrifugation of cells.

The device of the fourth embodiment includes an outer housing 400 having therein supporting elements 402, two membranes 404 (as described in U.S. Pat. No. 5,026,342 or U.S. Pat. No. 5,261,870) providing major faces which characteristics selected for the particular application, and supporting screens 408 of adequate strength and porosity for the same particular application (such as thawing of erythrocytes). One inside major face of the outer housing 400 incorporates one or more types and sizes of baffles 500 to distribute buffer entering the inflow chamber 502 of the device and to help to direct fluid through the membrane 404 forming the lower face of the inflow chamber 502 after the bypass tubes 504 are occluded by the clamp 506. The outflow chamber 508 may likewise be fitted with baffles (not shown). One end of the housing 400 has one or more tubes 510 leading to the inner chamber formed by structures 402, 404 and 408, and through which a suspension of cells 512 in buffer of appropriate composition and with appropriate cryoprotectants, as known to those skilled in the art, is placed. Another tube 514 later supplies additional buffer used for removal of cryoprotectant, as desired, with tube waste tube 516 providing egress when needed. The tubes are fabricated of suitable "sterile docking" materials known in the art. The unit is radiation sterilized (with tubes having been sealed) prior to use. The components may be made of virtually any material, preferably plastic or polymer. The two membranes 404 are fabricated from a porous membrane appropriate for the application, i.e., with composition, strength, pore diameter and percentage of pores being optimized for the particular application. The pores in the membranes are initially plugged as described in U.S. Pat. No. 5,026,342 and U.S. Pat. No. 5,261,870 with material which will maintain the pores in a plugged state during the interval required to fill the inner chamber with a suspension of cells (such as erythrocytes), to cool the contents to cryogenic temperature and to rewarm the cells to above 0° C. and for a desired interval thereafter (such as 5 to 10 minutes), but which will dissolve from the pores after 3–10 minutes exposure to buffer circulating across the membrane face in chambers 502 and 508.

Variations on the fourth embodiment include the possibility of the outer housing being a balloon or bladder structure itself, with any baffles being optional.

Figure 10A:
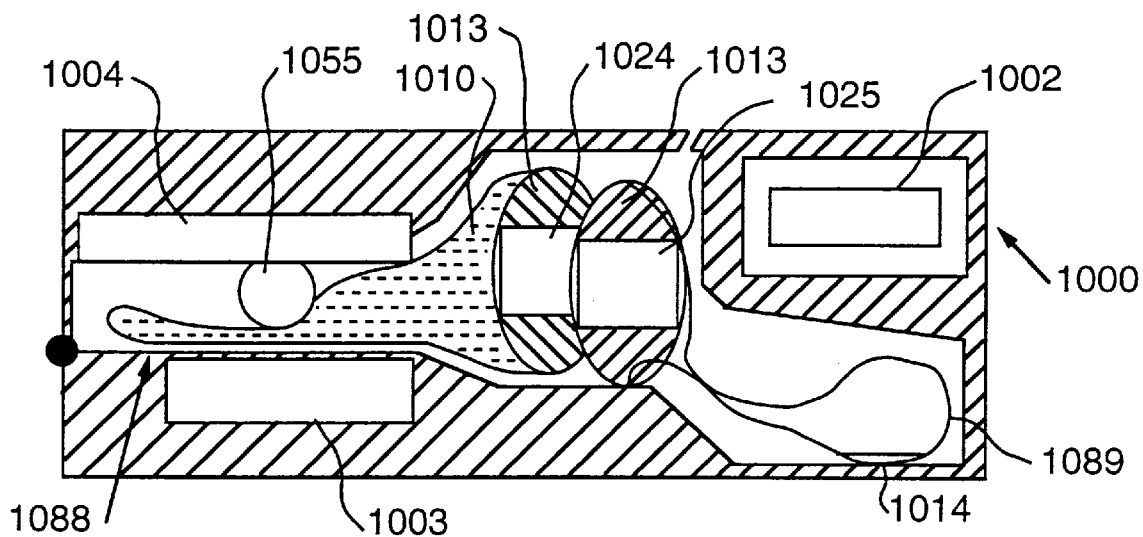
FIGS. 10a and 10b are side sectional views of a fifth embodiment of the present invention (with a detail inset).
Figure 10B:
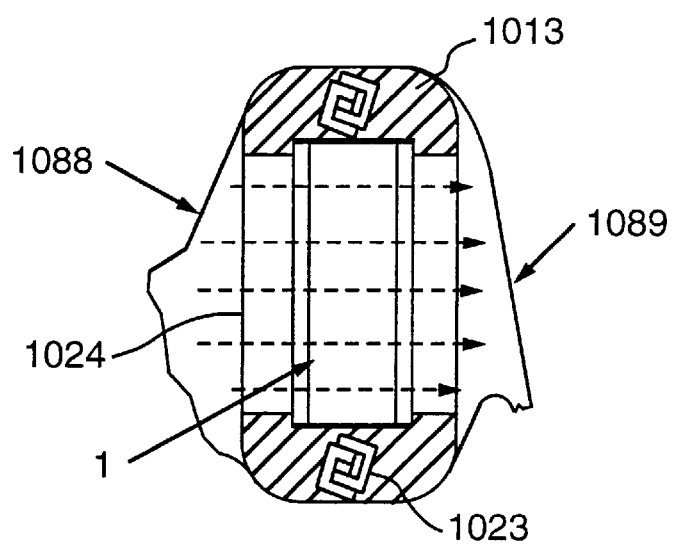
Figure 11:
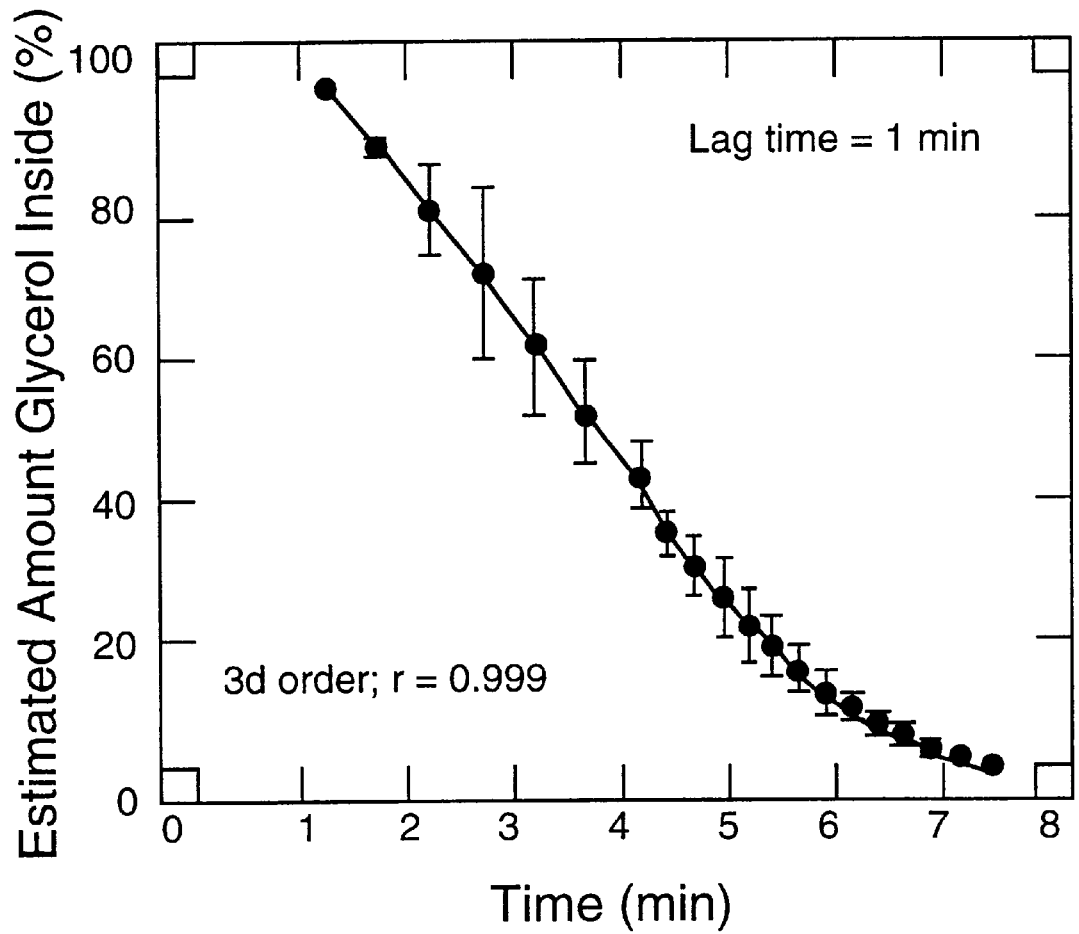

A fifth embodiment of the present invention appears in FIGS. 10a and 10b. A reusable housing 1000 incorporates a microprocessor controller 1002, a thermoelectric cooler 1003 and insulation (not shown). A linear stepping motor 1004 drives a roller or bar 1055 over a bladder 1088 containing buffer 1010, which is in turn connected to a port 1024 in one-half of the treatment chamber 1013. The treatment chamber 1013 is a two-part right cylinder, with a short height, in which each half represents a cylindrical structure having a cubic aperture therein, wherein when the two halves are adjoined via a locking mechanism the dual apertures hold a primary container 1 as shown in FIG. 1. The port 1025 in the other half of the treatment chamber 1013 is connected to a waste bladder 1089 containing waste buffer 1014. The primary container 1 would representatively have an internal volume of 0.5 to >5.0 ml, depending on the cell type and species, and preferably would be a thin (2.5 to 4.0 mm) rectangular, square, or cylindrical construct with the special membranes forming the major faces. In a further variation, the primary container 1 has a small port, sealed with UV glue after placing cells in the container before cooling, and a thin septum, punctured to remove cells after removal of cryoprotectant. Alternatively, a thin-walled tube, approximately 1 mm in diameter and as long as 10 or 15 mm, is used to fill the primary container 1, to provide a seal with a thermal bonding agent or adhesive plug, and to allow removal of cells after removal of cryoprotectant and cutting off the sealed portion where it protruded from the treatment chamber 1013.

To assemble the device according to the fifth embodiment of the invention, the two halves of the treatment chamber 1013 are locked around a primary container 1, by finger counter rotation and means of interlocking mechanisms 1023 shown in detail. Sterile buffer can then be brought to contact both membrane faces of the primary container 1 from the surrounding bladders 1010 and 1089. In practice, after a few minutes' exposure to the buffer, the pores open, and automatic activation of the stepping motor 1004 brings about controlled buffer circulation as described for the other embodiments of the invention, with the same controllable variability of pulse and flow.

The use of the devices disclosed herein improves the utility of containers including plugged pore membranes by coordinating buffer flow both to remove the pore plugs and to treat the contents of the container, and by providing pulsatile flow of buffer inducing turbulent flow and convective-dispersion within the primary container.

The invention is further illustrated by means of the ensuing example.

EXAMPLE 1

The device according to FIG. 2 was tested as follows. The inflow chamber 206 was pyramidal in shape, as was the outflow chamber 208. Buffer was moved through the device via a solenoid pump delivering 50 or 100 microliters per stroke, at a stroke frequency of 3–120 strokes per minute (computer controlled). The device was operated with the primary container 1 positioned so that its major faces—two opposing porous surfaces—were horizontal and the inflow chamber was below or above the primary container 1, or with the major faces vertical.

Initial tests monitored removal rates of glycerol from primary containers under various operating conditions (stroke volume, stroke rate, configuration and volume of the inflow and outflow chambers, starting glycerol concentration, presence or absence of bull or human sperm). Egress rates of glycerol from the primary chamber were controlled.

Figure 5:
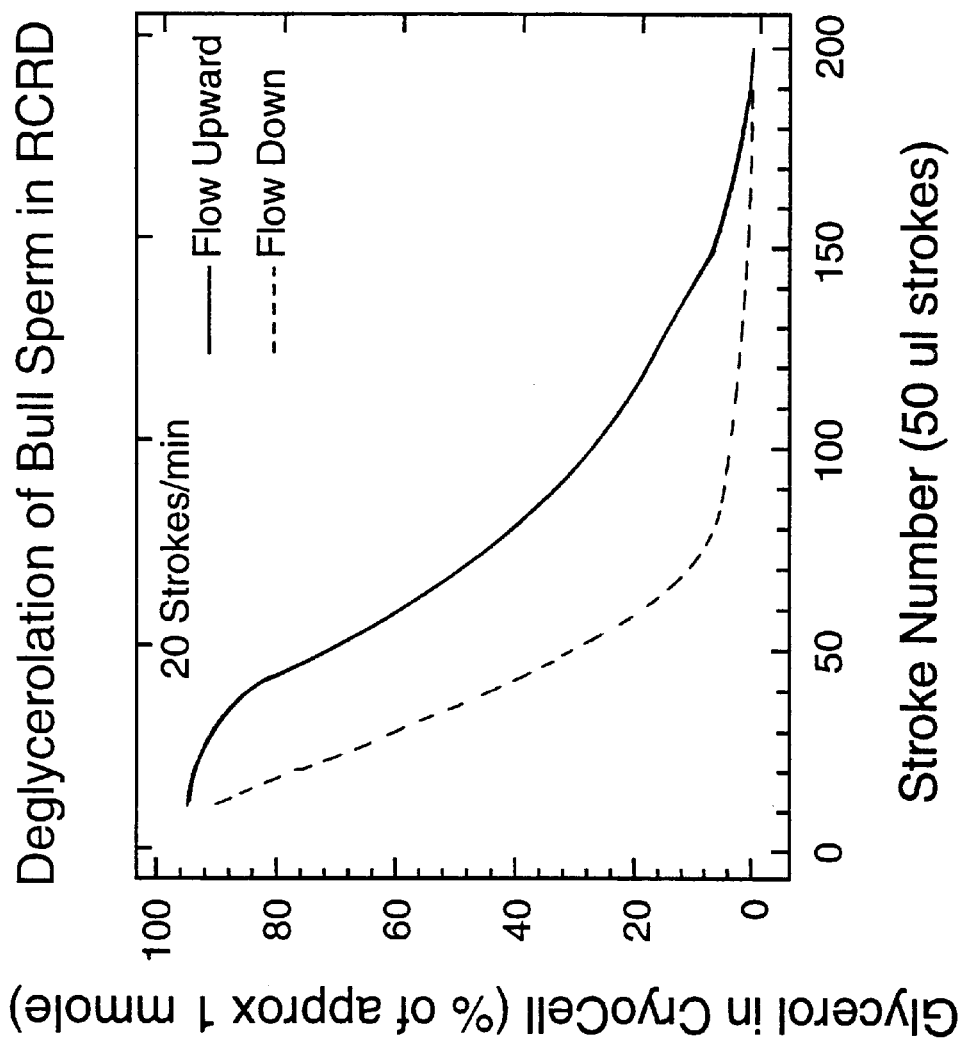
FIGS. 5–9 and 11 are graphic representations of test data regarding the present invention.
Figure 6:
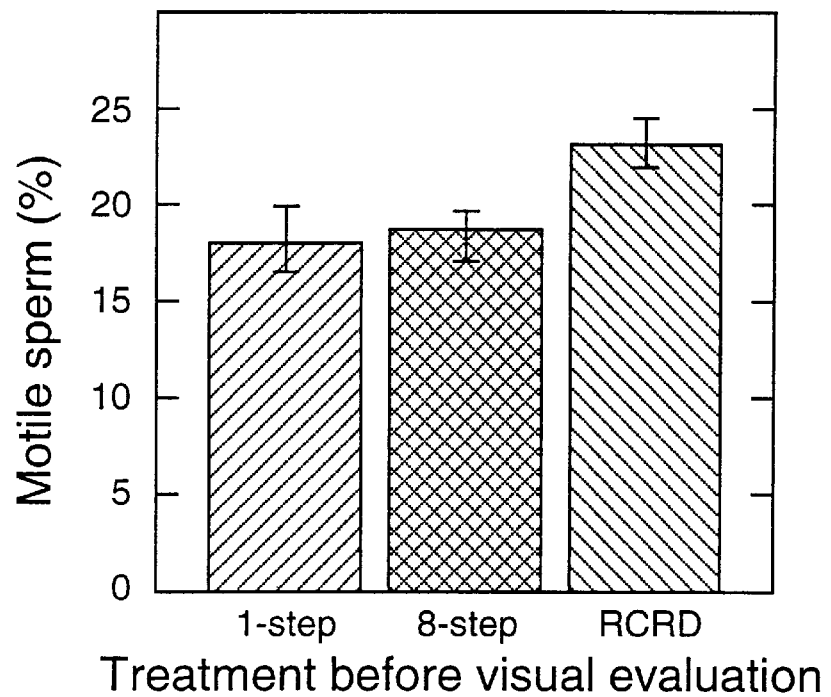
Figure 7:
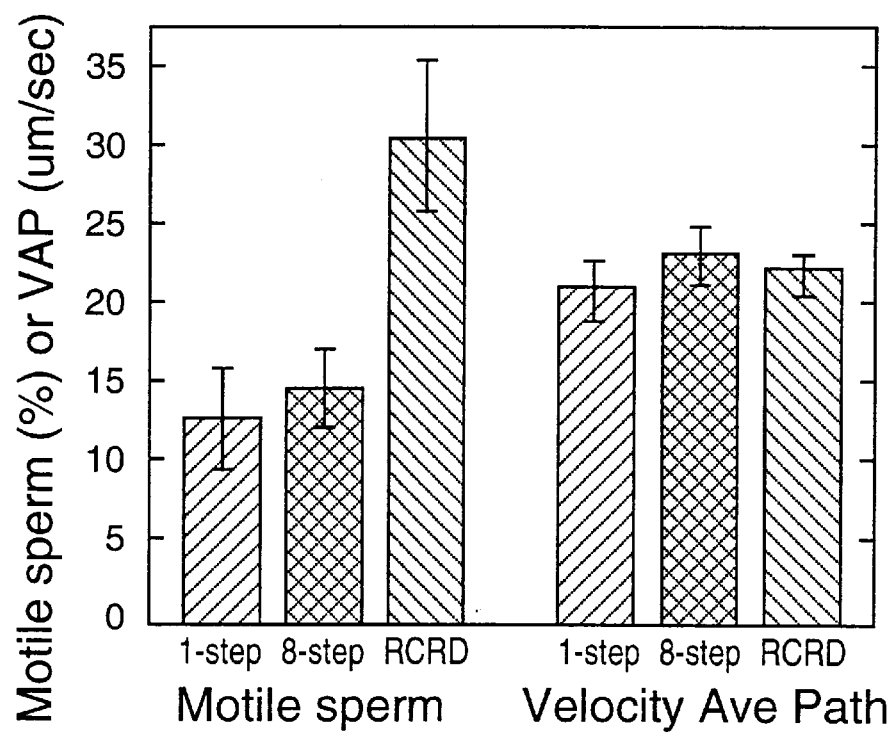
Figure 8:
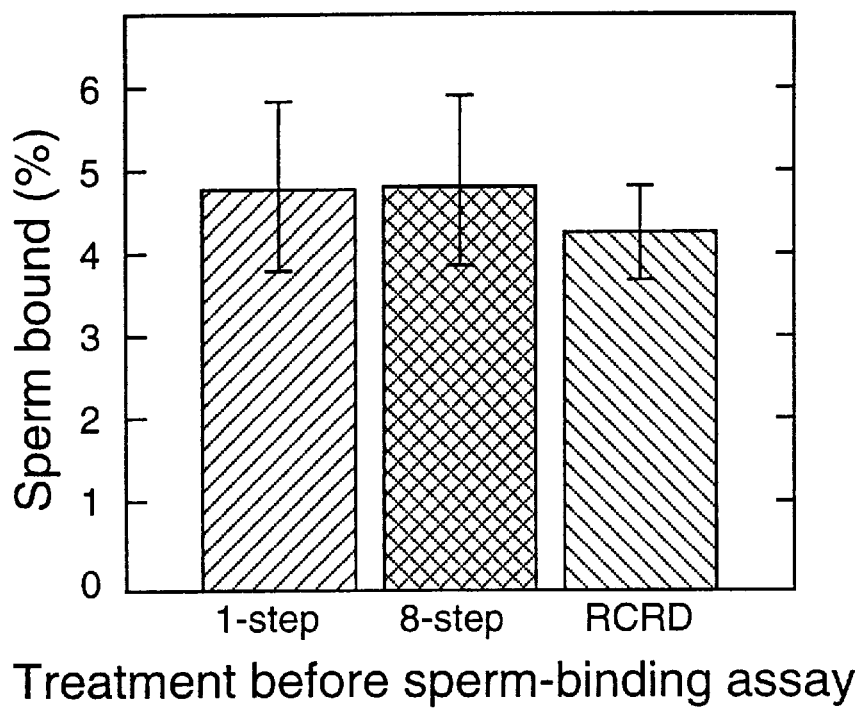
Figure 9:
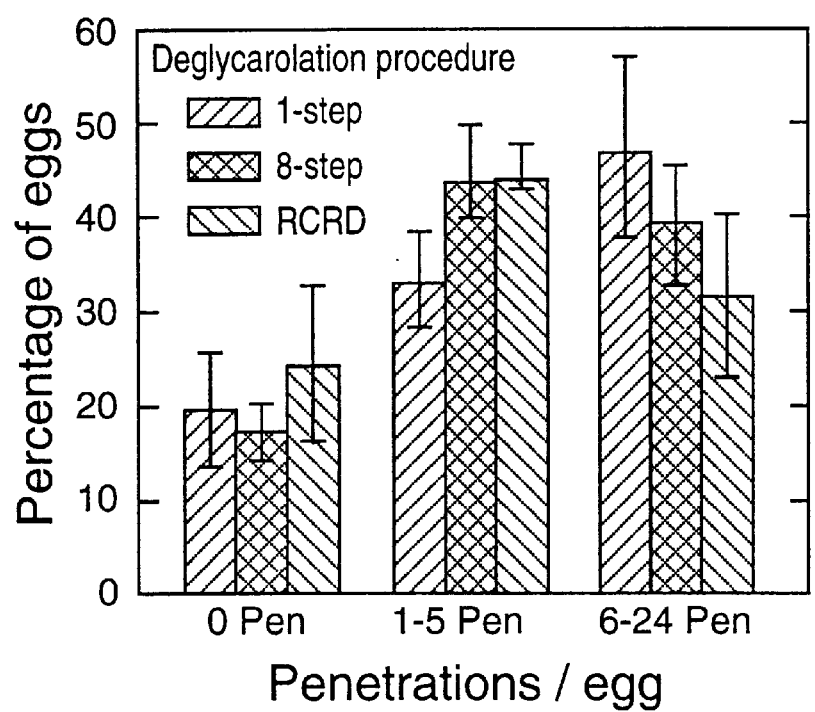

FIG. 5 shows removal rate of glycerol from a 1 ml primary container containing bull sperm (100 million) in buffer containing 0.88 M glycerol, averaged across 4 runs. A slower removal rate and evidence for more initial mixing with the primary container with upward flow, rather than downward flow, were evident. Definitive tests compared cryopreserved human sperm deglycerolated: (a) by conventional 1:10 dilution with buffer, followed by centrifugation at 350 times gravity for 15 minutes; (b) an 8-step process to achieve 1:10 dilution with buffer, followed by centrifugation at 350 times gravity for 15 minutes; versus (c) a rapid cryoprotectant removal device (RCRD) operated with the inflow chamber below the primary container. Evaluations of sperm quality, for cells deglycerolated by the 3 procedures, included percentage of motile sperm based on visual or computer-based analysis (using a Hamilton-Thorn Research, IVOS, system), percentage sperm bound to an egg membrane substrate (see U.S. Pat. No. 5,743,206), and penetration of zona-free hamster oocytes, using procedures known to those skilled in the art. Based on 8 replicate runs, 6.8 minutes were required to reduce glycerol concentration around the sperm to <0.03 M, whereas the prior art procedures required greater than 18 minutes to achieve the same result. FIGS. 6, 7, 8 and 9 show that the rapid cryoprotectant device shown in FIG. 2 provides sperm of equal or better quality than the 1-step or 8-step dilution methods of the prior art.

Although the invention has been described with particularity above, the invention is only to be limited insofar as is set forth in the accompanying claims.

We claim:

1. A method for removing a permeating substance from a suspension of one or more cells, comprising:

contacting one or more cells in suspension within a primary container with a permeating-substance-free buffer solution into which a permeating substance contained in said cells may diffuse; and exerting on said solution a repeating force creating an undulating motion of said solution in the area of said cells, wherein said repeating force creates a flow rate of at least 0.05 ml/min of a quantity of said solution into and through said primary container, and wherein said undulating motion of said solution improves removal of said permeating substance from said cells.

2. The method according to claim 1 wherein said permeating substance is a cryoprotectant, wherein said exerting step is completed within a period of about thirty minutes, and wherein said undulating motion further comprises a pulsatile flow which increases in frequency or volume throughout completion of the process.

3. The method according to claim 1 wherein said cells are spermatozoa or oocytes.

4. The method according to claim 1 wherein said cells are erythrocytes or other somatic cells.

5. The method according to claim 1 wherein said primary container is a container having two opposing porous surfaces therein.

6. A method for removing a cryoprotectant from a suspension of one or more cells, comprising:

contacting one or more cells in suspension with a solution into which a cryoprotectant contained in said cells may diffuse; and exerting on said solution a repeating force creating an undulating motion of said solution in the area of said cells, wherein said exerting step is completed within a period of about thirty minutes, said undulating motion comprising a pulsatile flow which increases in frequency or volume throughout completion of the process, wherein said undulating motion of said solution improves removal of said cryoprotectant from said cells.

7. A method for removing a permeating substance from a suspension of one or more cells, comprising:

contacting one or more cells in a suspension within a primary container with a permeating-substance-free buffer solution into which a permeating substance contained in said cells may diffuse;

wherein said permeating-substance-free buffer solution initially is external to said primary container, and said external buffer solution is moved through micropores in one wall of said primary container by exerting on said external buffer solution a repeating force creating a pulsatile flow of said permeating-substance-free buffer solution into said primary container and therein creating an undulating motion of said solution in the area of said cells, and excess mixed buffer is moved out of said primary container through micropores in another wall of said primary container;

wherein said repeating force creates a flow rate of at least 0.05 ml/min of a quantity of said solution into and through said primary container; and wherein said undulating motion of said permeating-substance-free buffer solution improves removal of said permeating substance from said cells.

* * * * *